United States Patent [19]
Striano

[11] Patent Number: 5,785,671
[45] Date of Patent: *Jul. 28, 1998

[54] LUMBAR SPINE SUPPORT

[76] Inventor: James S. Striano, 128 Brook Farm Rd., Bedford, N.Y. 10506

[21] Appl. No.: 683,033

[22] Filed: Jul. 16, 1996

[*] Notice: The term of this patent shall not extend beyond the expiration date of Pat. No. 5,489,260.

[51] Int. Cl.$^6$ .................................................. A61F 5/00
[52] U.S. Cl. .................... 602/14; 2/44; 128/96.1
[58] Field of Search ................. 602/19; 2/244, 2/311, 322, 325; 128/96.1, 100.1, 106.1, 107.1

[56] References Cited

U.S. PATENT DOCUMENTS

| | | | |
|---|---|---|---|
| 2,813,526 | 11/1957 | Beebe | 602/19 |
| 5,046,488 | 9/1991 | Schiek, Sr. | 602/19 |
| 5,105,806 | 4/1992 | Woodhouse et al. | 602/19 X |
| 5,257,419 | 11/1993 | Alexander | 602/19 |
| 5,310,401 | 5/1994 | Striano | 602/19 |
| 5,363,863 | 11/1994 | Lelli et al. | 602/19 |
| 5,489,260 | 2/1996 | Striano | 602/19 |

*Primary Examiner*—Jerome Donnelly
*Attorney, Agent, or Firm*—Charles J. Prescott

[57] ABSTRACT

Improved lumbar spine support including a posterior and an anterior panel for supporting the corresponding torso areas. These panels are connected by flexible fabric support belt arrangement for tightly surrounding the torso. The posterior panel preferably includes an elongated upright forwardly facing protrusion having a laterally extending wider lower portion for centering and securing the posterior panel over the lumbosacral area of the spine. The anterior panel, preferably slightly arcuate as seen from above, supports the abdominal musculature of the torso. A tightening strap arrangement connected to the support belt provides increased independent right and left side tightening of both panels against the torso.

2 Claims, 2 Drawing Sheets

LUMBAR SPINE SUPPORT

BACKGROUND OF THE INVENTION

1. Scope of Invention

This invention relates generally to body torso supports, and more particularly to a semi or substantially rigid orthosis which provides unique lumbar centering and abdominal lifting features.

2. Prior Art

Devices in the form of rigid, semi-rigid, or flexible material constructed to at least partially surround the lower back region of the human torso are well-known for the treatment and rehabilitation of spinal disfunction. One such device is shown in U.S. Pat. No. 4,508,110 to Modglin which discloses a body jacket constructed in two parts to be laced together into a final adjusted position and then easily installed and removed thereafter.

Another device known to applicant is shown in U.S. Pat. No. 4,696,291 invented by Tyo directed to a device for treating lower back pain comprising three generally rigid members which, when properly installed, are claimed to apply a centrally directed beneficial force to the abdomen and the gluteal muscles. Rowe in U.S. Pat. No. 4,930,499 teaches a sacral brace intended for comfortable extended wear including a rigid posterior sacral pad having a vertical central channel and connectable to an abdominal leverage plate provided for anchoring the sacral pad by tying straps.

A simple brace and method of application is disclosed in U.S. Pat. No. 5,074,292 to Cox for immobilization of various regions of the torso.

The Triplett U.S. Pat. No. 2,541,487 discloses a spinal brace including a main metal frame having a pair of upright bars which are co-extensive and spaced apart to define an open central area positionable along the spine of the user.

Three previous patents for which I am the inventor are also disclosed, those patents being U.S. Pat. Nos. 5,207,636, 5,310,401, and 5,489,260. However, none of my prior patents disclose either a floating form-fitted posterior shell encased within a loosely fitted covering, the forwardly facing sheet of which is formed of a compressible foam layer or the utilization of an arcuate anterior panel connected within one of the overlapping strap portions for abdominal support.

The present invention provides a lumbar spine support comprised of a posterior panel or section to accommodate the bony prominences known as the posterior superior iliac spine (PSIS), the iliac crest and the lumbosacral spine. The posterior panel preferably includes an upright forwardly protrusion with an oblong shaped transverse bottom portion conforming to the skeletal cavity created at the junction of the lumbar vertebra and the sacrum and pelvis serving to guide the placement of the posterior panel to insure centering over the spine and locking onto the lumbosacral area to facilitate appropriate dispersion of the lower abdominal resistive force when the adjustable closure system is tightened. An anterior panel is positioned adjacent a distal end of one of two flexible straps which overlap to retain the device in operative position around the torso. The anterior panel presses against and supports the abdominal area of the torso.

BRIEF SUMMARY OF THE INVENTION

This invention is directed to an improved lumbar spine support including a posterior and an anterior panel for supporting the corresponding torso areas. These panels are connected by flexible fabric support belt arrangement for tightly surrounding the torso. The posterior panel preferably includes an elongated upright forwardly facing protrusion having a laterally extending wider lower portion for centering and securing the posterior panel over the lumbosacral area of the spine. The anterior panel, preferably slightly arcuate as seen from above, supports the abdominal musculature of the torso. A tightening strap arrangement connected to the support belt provides increased independent right and left side tightening of both panels against the torso.

It is therefore an object of this invention to provide an improved lumbar spine and abdominal support device which combines the biomechanical advantages of a posterior and an anterior support panel with the comfort and convenience of a two-stage and fully adjustable closure system.

It is yet another object of this invention to provide a lumbar spine support which causes improved hydrostatic lift to occur in the abdominal cavity to relieve the pressure on and to allow equalization of, the discs of the spine.

It is still another object of this invention to provide a lumbar spine support which, by hydrostatic lift, overcomes the forces of gravity and resists reversing chiropractic adjustments caused by twisting, turning or poor ergonomics.

It is yet another object of this invention to provide a lumbar spine support which is firmly self-positioning on the PSIS, the iliac crest, and the lumbosacral spine to control lumbosacral rotation, thus lessening the possibility of reinjury during healing.

It is still another object of this invention to provide a lumbar spine support which will adequately support the spine while permitting exercising of the underlying musculature and is of an ultra thin construction to facilitate undergarment wear.

In accordance with these and other objects which will become apparent hereinafter, the instant invention will now be described with reference to the accompanying drawings.

DETAILED DESCRIPTION OF THE INVENTION

Figure 1:
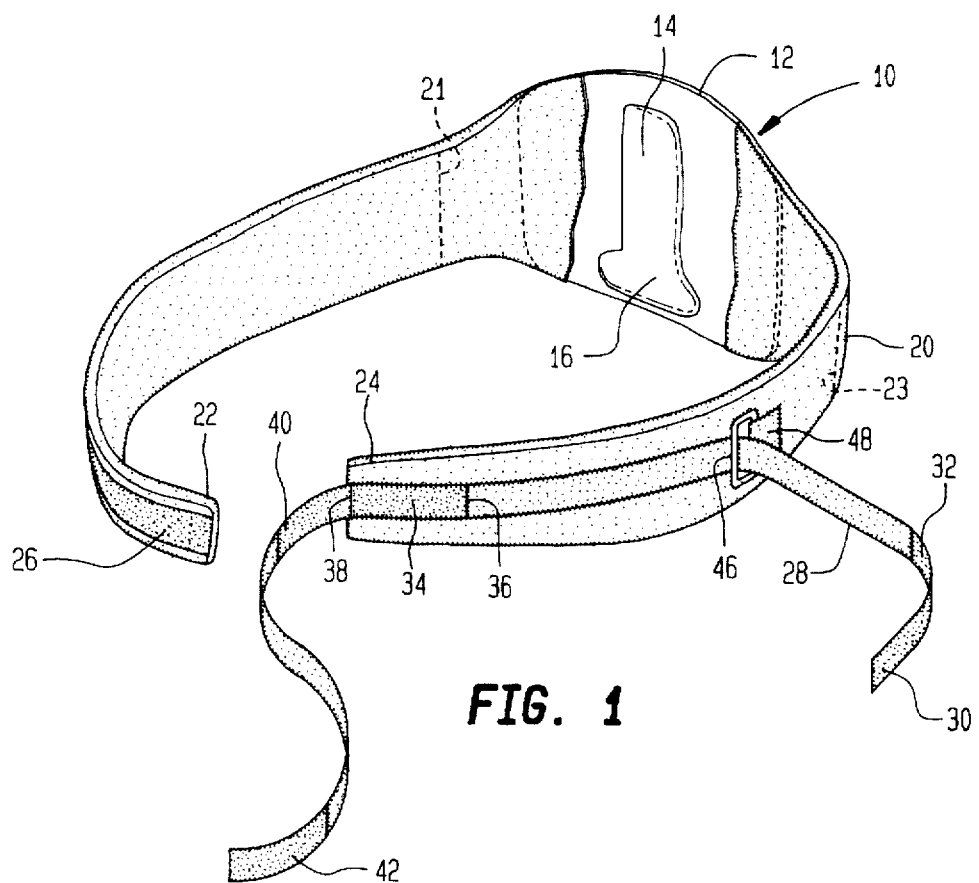
FIG. 1 is a left side perspective view of the invention.
Figure 2:
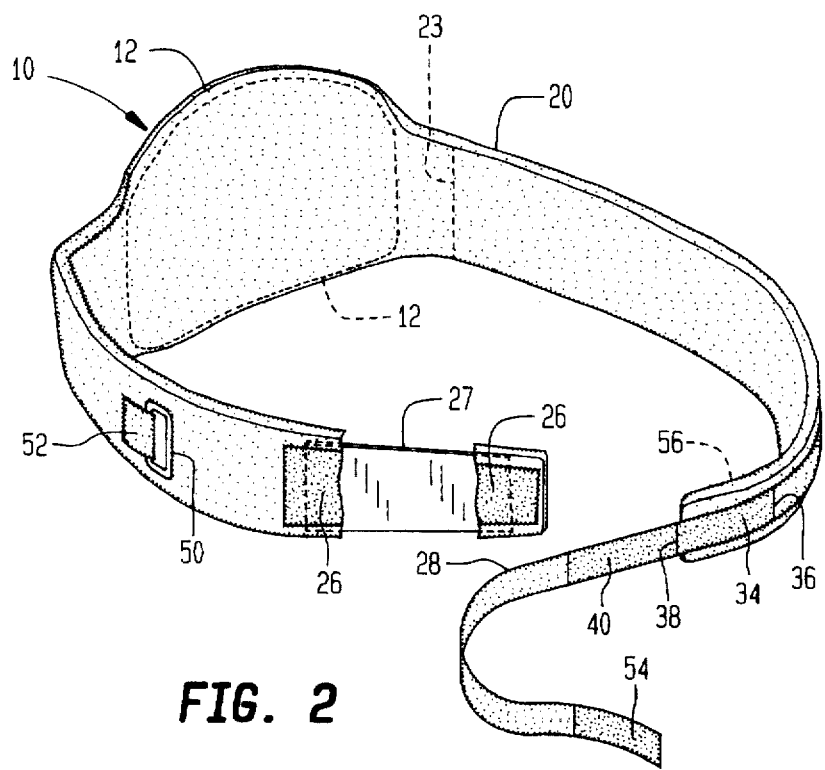
FIG. 2 is a right side perspective view of the invention.

Referring now to the drawings, the invention is shown generally at numeral 10 in all figures and includes a posterior panel 12 which is fabricated of a contour-molded sheet of thermo-plastic material. This posterior panel 12 is semi-rigid in that some flexure is possible to improve fit and comfort during normal body movement.

The posterior panel 12 includes an elongated, upright protrusion 14 formed inwardly into the thermal plastic outer layer of panel 12. This protrusion 14 includes a lower elongated transverse portion 16, the combination structured, when the posterior panel 12 is positioned as shown in FIG. 4, to guide the placement of the posterior panel 12 for proper centering over the spine and to lock onto the lumbosacral area of the spine for even dispersion of resilient force when tightly strapped against the posterior torso of the patient.

Figure 5:
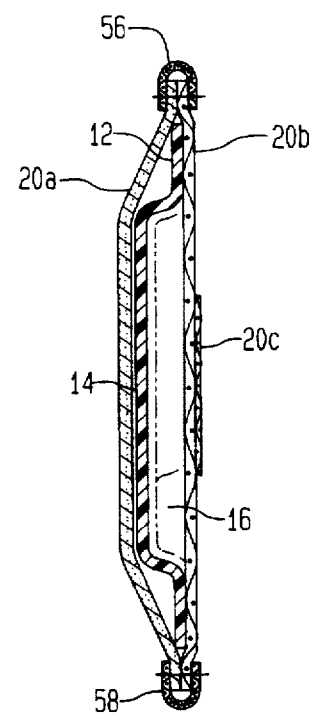
FIG. 5 is a section view in the direction of arrows 5—5 in FIG. 3.

As best seen in FIG. 5, the anterior panel 12 is encased loosely within flexible rear fabric panel 20b and compressible foam forward panel 20a. These two panels 20b and 20a, which form the back portion of a fabric support belt 20, are sewn together along their side margins 21 and 23 and upper and lower margins 56 and 58, respectively, having finishing tape concealing these sewn margins. The forwardly foam panel 20a importantly provides substantial improved comfort without limiting the effectiveness of self-aligning features of protrusion 14 above described. Reinforcing strap 20c reduces undesirable elongation or elasticity of the support belt 20 across the torso posterior.

Figure 4:
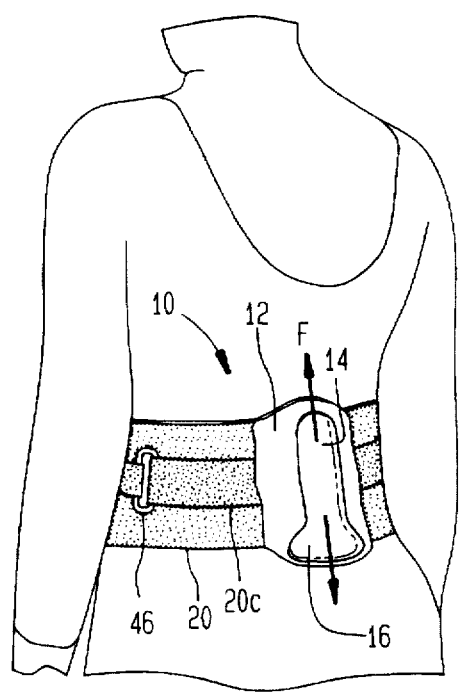
FIG. 4 is a perspective view of the invention in use as viewed from the rear of a user.

After the posterior panel 12 is initially positioned against the posterior torso area as shown in FIG. 4, free ends of the flexible fabric support belt 20 are drawn forwardly and around the lower abdominal area of the front of the torso so as to overlap one another and to be so held by self-engaging hook and loop material 26 and 56. A loop or ring 46 and 50 is secured by stitched-in-place fabric 48 and 52, respectively, adjacent to the posterior shell 12. A flexible tightening strap 28, is secured at a mid region 34 thereof by stitching 36 and 38 against an end portion 24 of the outer surface of support belt 20. One end of the tightening strap 28 is fed through loop 46 back along, and secured against itself at 36 by a releasible attaching means such as hook and loop (VELCRO) arrangement 32/34.

The other end 54 of the tightening strap 28 extends around the left side of the torso and support belt end portion 26 to be feed through and interengage with loop or ring 50 and then be drawn back forwardly around the left side of the torso to be engaged against itself at 40/42.

Figure 3:
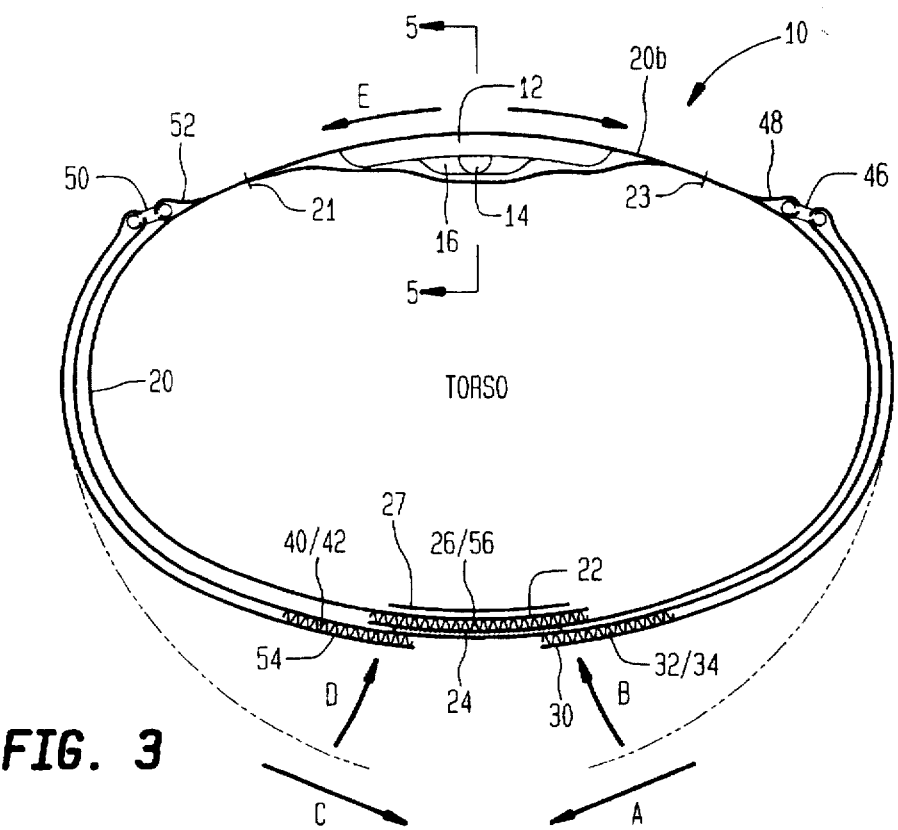
FIG. 3 is a top plan simplified schematic view of the invention in position around a user's torso.

Thus, the distal ends of support belt 20 are first overlapped and tightened and releasibly secured together by self-engaging hook and loop surfaces 26/56 against the lower abdominal area of the torso as seen in FIG. 3 to secure a desired tensioning. To further increase tensioning, the distal ends 30 and 56 of tightening strap 28 are first pulled in the direction of arrows A and C, respectively, either simultaneously or separately. When the desired increased tension is achieved, each end 30 and 54 is moved in the direction of arrows B and D, respectively, for releasible attachment back on itself by hook and loop surfaces 32/34 and 40/42. By appropriate two-stage tensioning of the arrangement in this manner, the upright protrusion 14 of posterior shell 12 serves to center and align the entire arrangement so as to properly stabilize the lower spine area from excessive movement.

A semi-flexible anterior support panel 27 is also provided and is connected between the inner and outer layers of the flexible fabric layers of one support belt end portion 26. This anterior panel 27 is formed of flat plastic sheet material being preferably slightly arcuate as viewed from above. It's positioning within belt end portion 26 is such that, as best seen in FIG. 3, positioning of this anterior panel 26 is against the abdominal region for abdominal musculature support and hydrostatic lifting thereof. As such, the anterior panel 27 is viewed as "floating" in that it has no specific orientation means, but rather is positioned as determined by either the user or the medical practitioner prescribing the device to obtain desired abdominal support and comfort.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A lumbar spine support comprising:

a substantially rigid, body contoured, continuous posterior panel having right and left lateral edges which are sized and positionable to terminate near the right and left posterolateral regions, respectively, of a torso of a patient;

a flexible support belt connected to said posterior panel and sized to extend forwardly from said posterior panel around the torso;

a right and a left end of said support belt overlapping and connectable against one another for providing a first stage of adjustably tightening said posterior panel against the torso;

a flexible tightening strap connected at a mid region thereof adjacent to one said end of said support belt and extending in either direction along said support belt;

a pull ring connected to said support belt adjacent each said right and left lateral edges of said posterior panel;

said tightening strap sized in length for each end thereof to pass through one said pull ring, each said tightening strap end doubling back for releasible connection against itself;

said tightening strap providing a second stage for increasably tightening said posterior panel against the torso; a separate anterior panel embedded within and generally coextensive with an end portion of one said support belt whereby said anterior panel is positionable over, and supports, an abdominal musculature of the torso.

2. A lumbar spine support as set forth in claim 1, wherein:

said posterior shell includes an elongated central upright protrusion extending forwardly from the continuous surface of said posterior panel having a laterally extending portion at the lower end thereof sized for being positioned and structured to center said posterior shell over the lumbosacral area of the spine wherein said protrusion provides even dispersion of a resilient force;

said upright protrusion structured, in cooperation with said posterior shell, to conform to the skeletal cavity created at the junction of the lumbar vertebra and the sacrum.

* * * * *